United States Patent [19]

LeMay

[11] 4,398,251
[45] Aug. 9, 1983

[54] RADIOGRAPHY

[75] Inventor: Christopher A. G. LeMay, Osterley, England

[73] Assignee: EMI Limited, Hayes, United Kingdom

[21] Appl. No.: 822,817

[22] Filed: Aug. 8, 1977

Related U.S. Application Data

[63] Continuation-in-part of Ser. No. 716,566, Aug. 23, 1976, Pat. No. 4,088,887, which is a continuation of Ser. No. 639,478, Dec. 10, 1975, Pat. No. 4,010,371.

[51] Int. Cl.³ ............................................. A61B 6/00
[52] U.S. Cl. .................................... 364/414; 378/901
[58] Field of Search ......................... 250/252, 445 T; 364/414; 378/901

[56] References Cited

U.S. PATENT DOCUMENTS

| | | | |
|---|---|---|---|
| 3,881,110 | 4/1975 | Hounsfield et al. | 250/445 T |
| 3,924,129 | 12/1975 | LeMay | 250/336 |
| 4,002,910 | 1/1977 | LeMay | 250/445 T |
| 4,010,371 | 3/1977 | LeMay | 250/445 T |
| 4,051,378 | 9/1977 | Krippner | 250/445 T |
| 4,088,887 | 5/1978 | LeMay | 250/445 T |
| 4,149,247 | 4/1979 | Pavkovich et al. | 364/414 |
| 4,149,248 | 4/1979 | Pavkovich | 364/414 |
| 4,149,249 | 4/1979 | Pavkovich | 364/414 |

OTHER PUBLICATIONS

James et al., *Mathematics Dictionary*, Revised Edition, The Digest Press, Van Nuys CA 1946, Title Page, pp. 116, 117, and 138.

*Primary Examiner*—Alfred E. Smith
*Assistant Examiner*—T. N. Grigsby

[57] ABSTRACT

A CT scanner is disclosed in which sets of X-radiation measurements, each set being for a fan-shaped distribution of beam paths, are used by a convolving circuit as though they were for sets of parallel beam paths. The inaccuracies due to this are countered by using correction factors, one for each pixel of the final picture of the patient slice, which correction factors are derived by the use of a phantom of known X-ray response. In addition, a special interpolation technique is disclosed to facilitate accurate back projection.

11 Claims, 8 Drawing Figures

RADIOGRAPHY

REFERENCE TO A RELATED APPLICATION

This application is a continuation-in-part of co-pending patent application Ser. No. 716,566 now U.S. Pat. No. 4,088,887, filed Aug. 23, 1976 in the name of the same inventor as a continuation of application Ser. No. 639,478, filed Dec. 10, 1975 and now U.S. Pat. No. 4,010,371.

This invention relates to a method of and apparatus for constructing a representation of the variation of absorption of a planar slice of a body with respect to penetrating radiation such as X- or γ- radiation.

In U.S. Pat. No. 3,778,614 methods of and apparatus for constructing such a representation are described. According to one example described in that specification, a suitable source of radiation provides a pencil beam of radiation and a suitable detector is arranged to provide a measure of the absorption suffered by the beam in passing through the body. The source and detector are each provided with a scanning movement, relative to the body, to provide such a measure of absorption for each of a plurality of substantially parallel pencil beams of radiation at each of a plurality of inclinations in the plane of the slice. Those measurements of absorption are then processed by suitable means to provide a distribution of linear absorption coefficients for the said slice. To provide the required plurality of beams the source and detector are reciprocated in the plane of the slice and orbited in steps about a common axis normal to that plane.

The processing described in the aforementioned specification is such that the finally displayed distribution of absorption coefficients is the result of successive approximations. In U.S. Pat. No. 3,924,129 there is described an apparatus for processing the derived absorption data signals in which the successive approximations are made by a convolution method in which the final display of the absorption distribution can be produced more rapidly than by the procedure of the said U.S. Pat. No. 3,788,614.

In U.S. Pat. No. 3,946,234 there is described a variation of the apparatus of the said U.S. Pat. No. 3,778,614 for the same purpose, in which a source of radiation is arranged to provide a beam of radiation which has a wide angular spread in the plane of the slice. That beam is divided into a plurality of pencil beams by suitable collimators and an array of detectors is provided to measure the intensity of each of those beams after passage through the body. Scanning motions as described hereinbefore are further imposed on the source and detectors. As a result of the reciprocating movement the array of detectors provides absorption information relating to a plurality of sets of parallel beam paths followed by the radiation, the sets being angularly spaced by the angular separation of the beams. Thus the orbital step between each reciprocating movement may be through a relatively larger angle. That variation of the apparatus is therefore capable of providing a faster scanning movement than that of the said U.S. Pat. No. 3,778,614. However, for the examination of certain parts of the body it is desirable to further increase the scanning rate. A substantial increase in scanning rate is however made difficult by the requirement that the orbital movement should be intermittent.

The application of a convolution function to a set of output signals which are measured by the response encountered by X-radiation in travelling along a set of planar spaced paths, implies that the paths are parallel, the path spacing from a reference path being a parameter of the convolution function. However, if the paths are not parallel, the path spacing is not single valued but varies along the lengths of the paths. Nevertheless, if the total deviation from parallelism over the entire set is restricted, an invariant convolution function can be employed without significant error, as described in U.S. Pat. No. 4,010,371. This restriction applies, however, only when no corrective procedure is employed, and an object of this invention is to provide a simple method and apparatus for reducing significant errors which are liable to arise in the general application of convolution to sets of output signals which are related to sets of paths which deviate from parallelism.

Apparatus is known, for example, from U.S. Pat. No. 4,035,647, which is capable of even higher scanning rates than are achievable by the techniques described hereinbefore. However, the rapid scanning is achieved by a process which tends to produce data in groups relating to beam paths fanning out from a source or fanning into a detector and of considerable total divergence in angle.

It is another object of this invention to permit convolution processing of the kind described in said U.S. Pat. No. 3,924,129 to be applied to the group of data provided by such apparatus.

It is a further object of this invention to avoid the need to sort such data into groups relating to sets of parallel beam paths and to compensate for inaccuracies produced by such sorting.

It is a still further object of the invention to avoid the need for complex and time consuming processing procedures to render data relating to divergent beam paths compatible with said convolution processing.

In order that the invention may be clearly understood and readily carried into effect, embodiments thereof will now be described with reference to the accompanying drawings of which:

Figure 3:
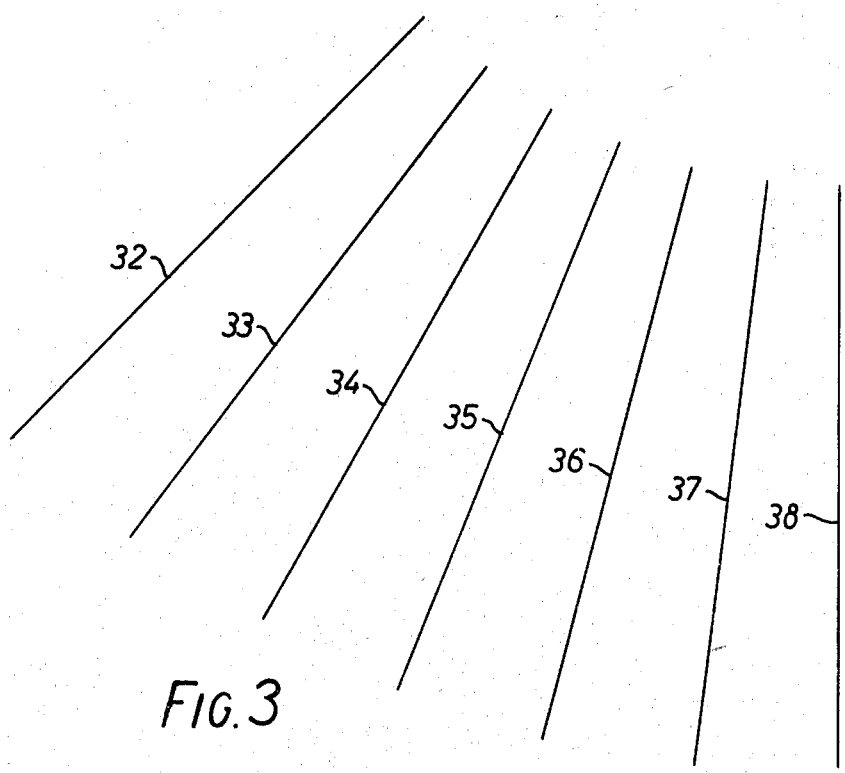
FIG. 3 is used to explain the principle of the invention.
Figure 4:
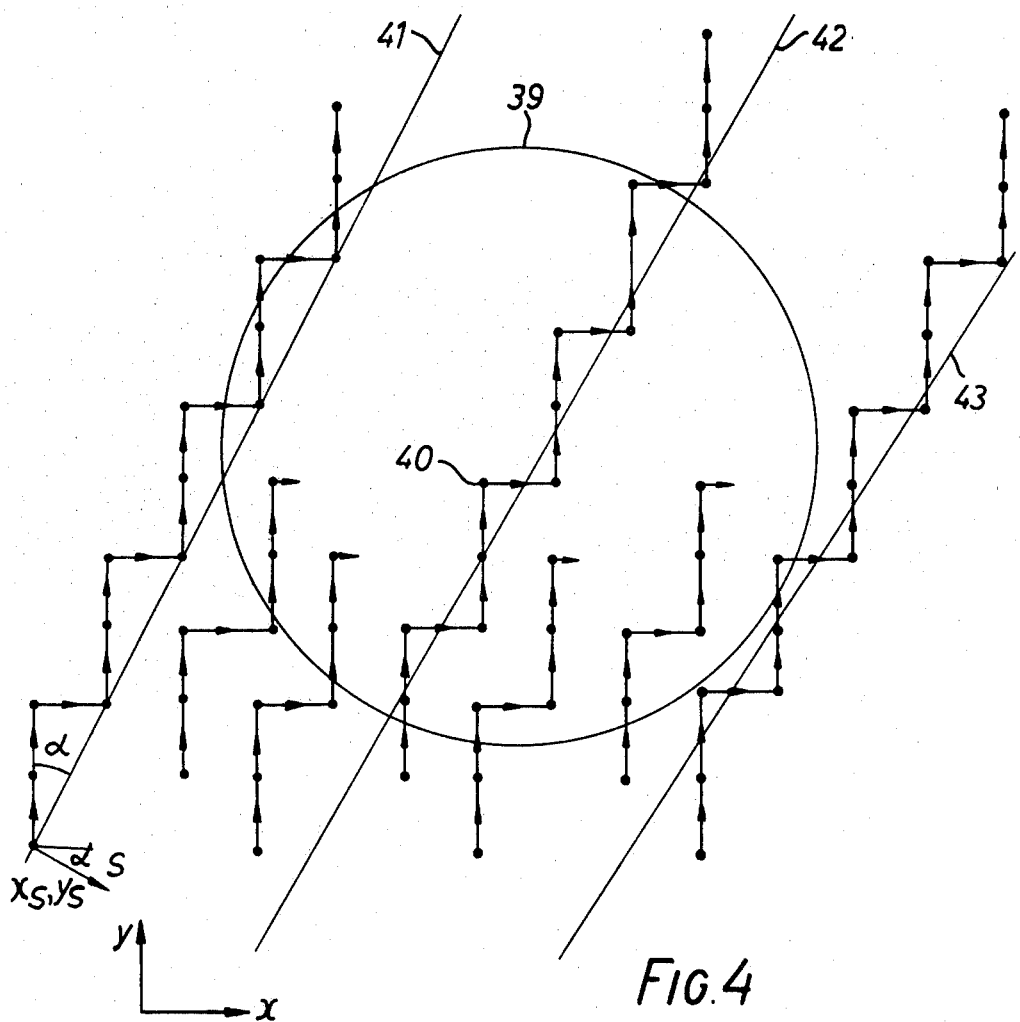
FIG. 4 illustrates a method of organising the data obtained.
Figure 5:
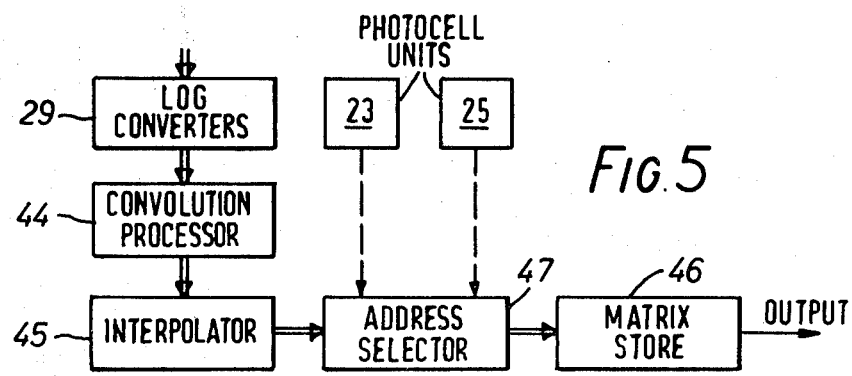
Figure 6:
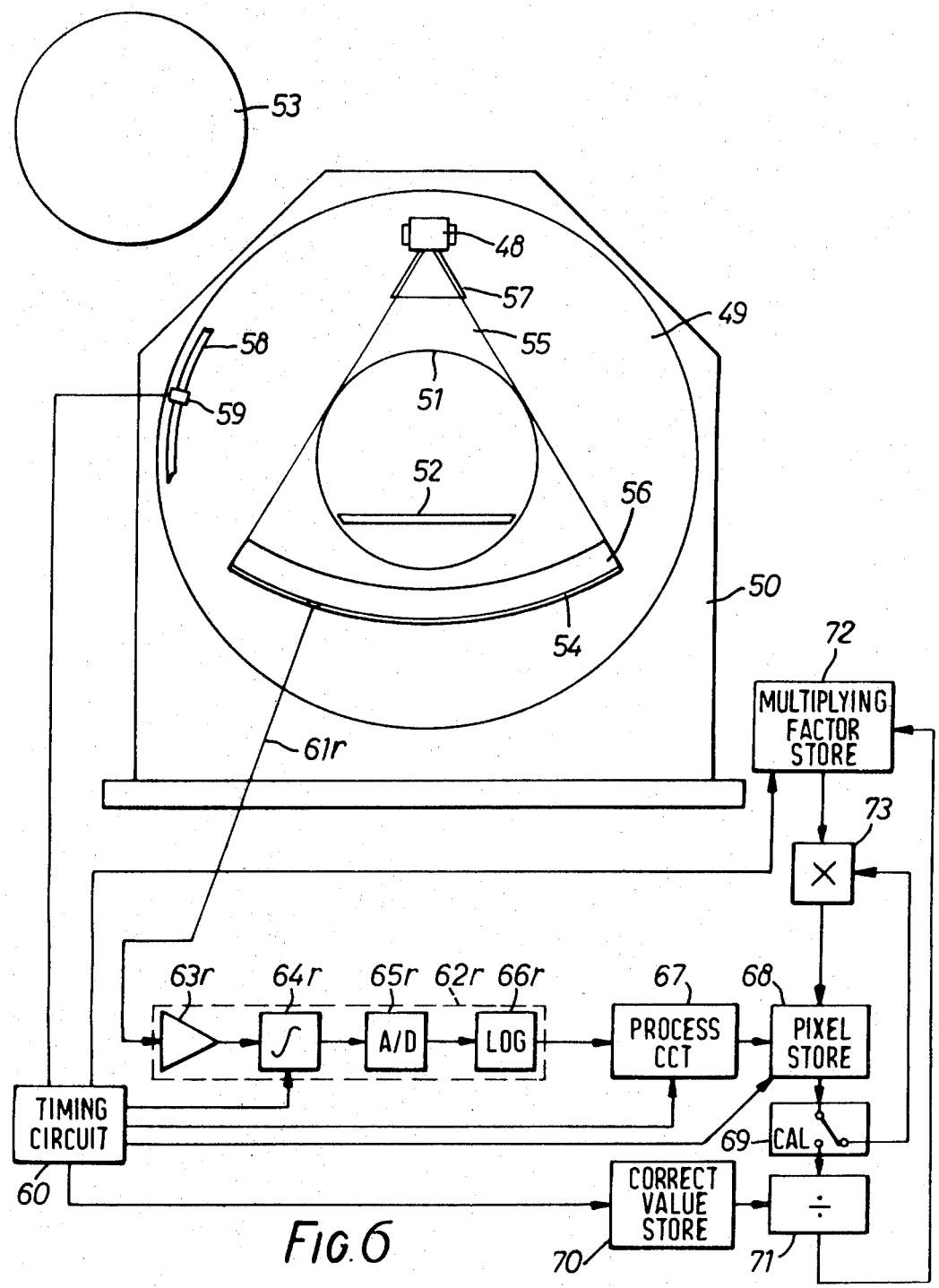
Figure 7:
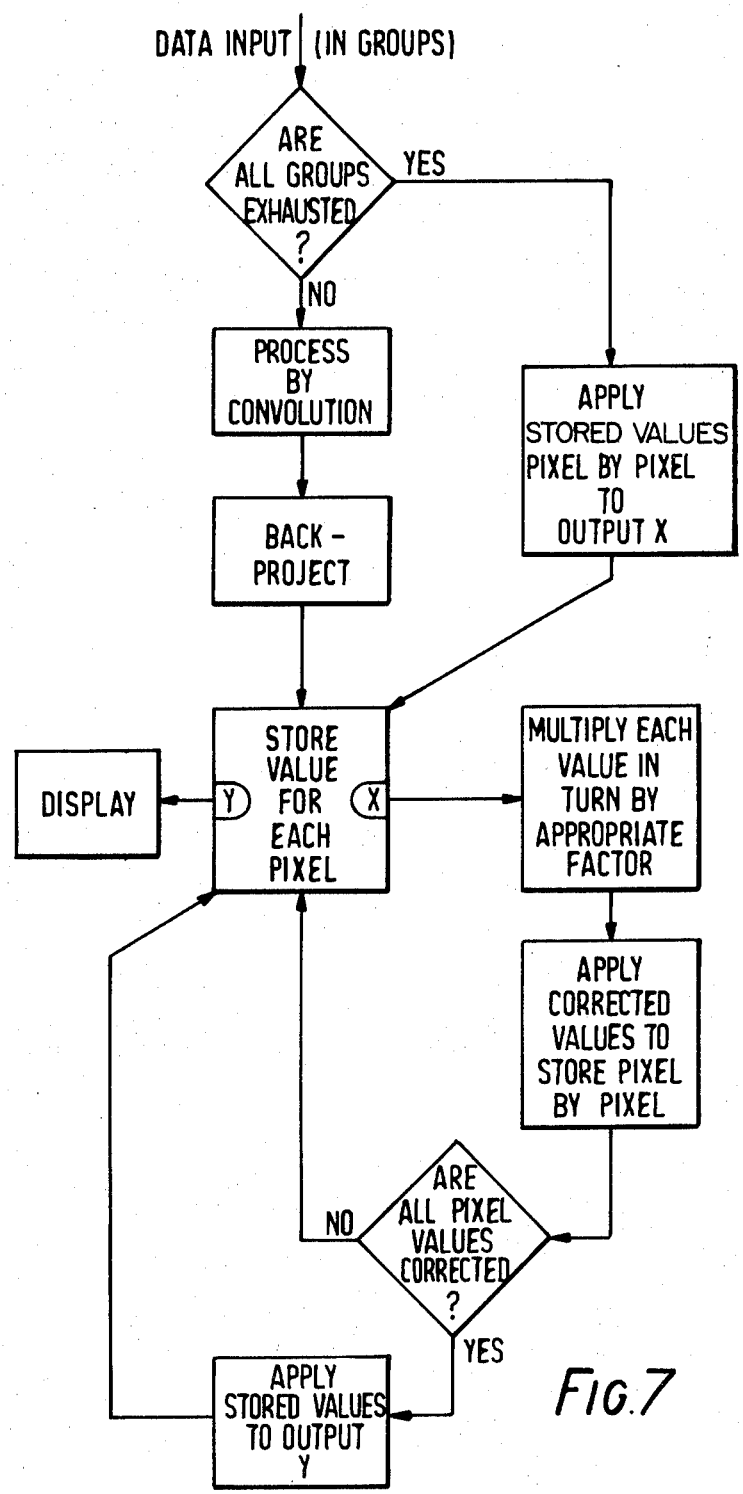

FIG. 5 shows in block diagrammatic form a processing arrangement for use with the example of the invention described with reference to FIGS. 1–4, FIG. 6 shows, in plan view and partly in block diagrammatic form, a radiographic apparatus in accordance with another example of the invention, FIG. 7 shows, in flow diagrammatic form, one way in which an example of the invention can be carried out, and FIG. 8 shows, in schematic plan view, another kind of radiographic apparatus to which the invention is applicable.

As described hereinbefore, a requirement for a stepped orbital movement is one factor limiting the scanning rate of the aforementioned apparatus. In the arrangement to be described with reference to FIGS. 1–5, the stepped movement is replaced by a continuous orbital motion so that the required data can be obtained at an increased rate.

Figure 1:
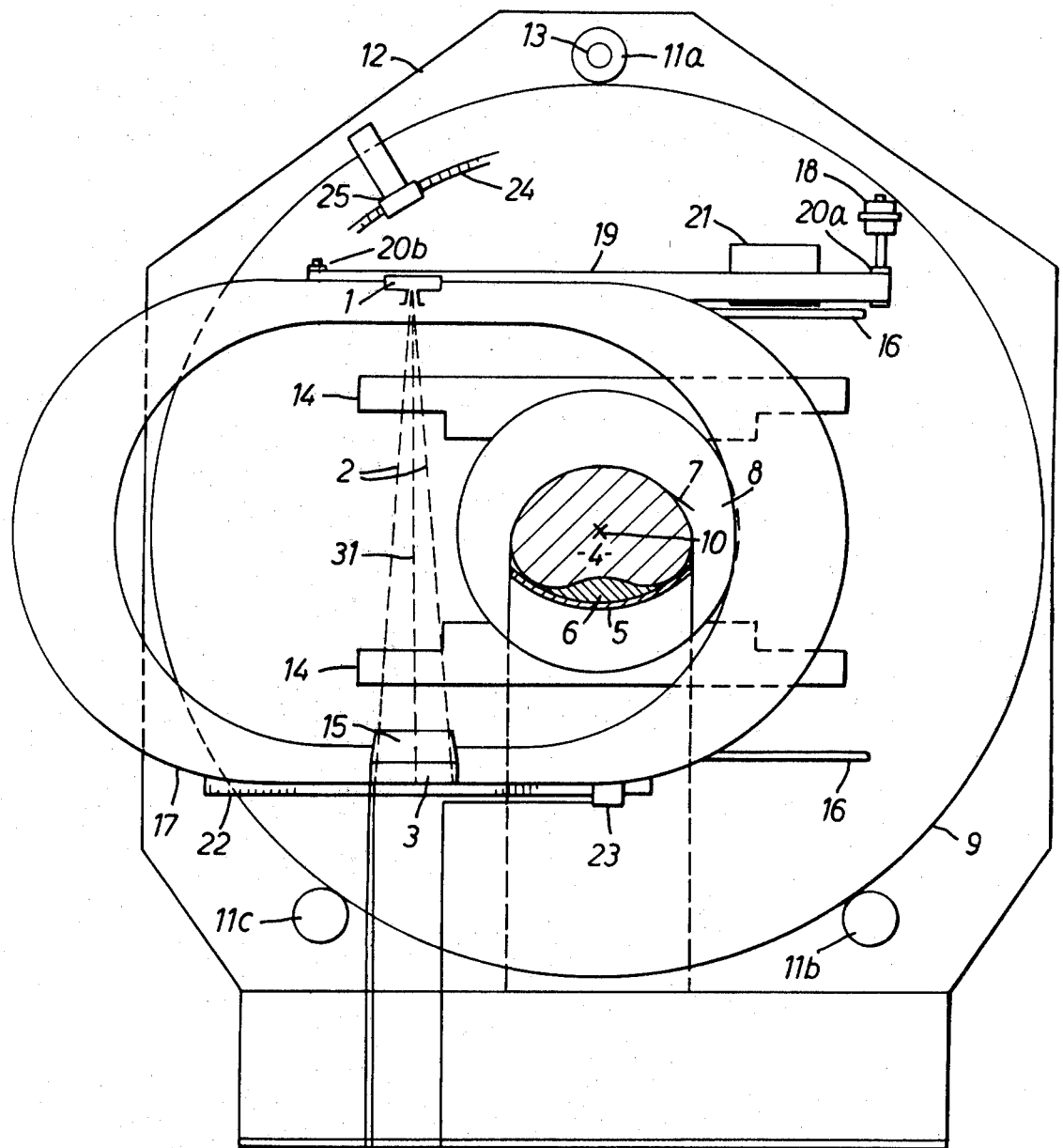
FIG. 1 shows an apparatus suitable for use with one example of the invention.
Figure 1:
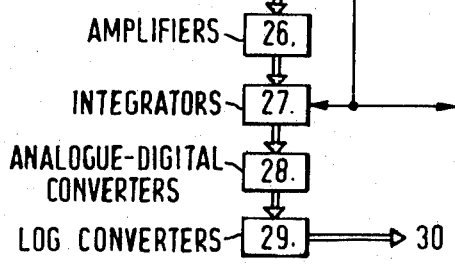

Referring now to the drawings, FIG. 1 shows in end elevation an apparatus of the type described in the aforementioned U.S. Pat. No. 3,946,234 adapted for use with continuous rotation. A source 1 directs a fan-shaped spread of radiation 2 towards a bank of detectors 3. The source 1 may be a rotating anode tube of known type to be as light as possible for a conventional source and the detectors 3 may be of any suitable kind such as scintillation crystals with associated photomultipliers.

A body 4, of a patient to be examined, is supported on a suitably shaped bed 5. A material 6, having an absorption similar to that of body tissue is positioned between the body 4 and the bed 5 to substantially exclude air from the gap therebetween and is extended partly about the body to provide an approximately circular cross-section to examining radiation.

The body is retained firmly in a desired positioned by means such as a restraining strap 7. If desired more rigid means may be provided to hold the body, for example, a two-part rigid ring attached to bed 5.

The bed 5 and body 4 are inserted into an aperture 8 in a rotatable member 9 on which source 1 and detectors 3 are mounted. The rotatable member 9 is arranged to rotate about an axis 10 central to aperture 8 and perpendicular to the paper. For that purpose it is supported on three gear wheels 11a, b, and c which engage with teeth, not shown, cut into the periphery of member 9. The gear wheels 11 are journalled in a main frame 12 of the apparatus, which may be of any form suitable to support the rotating parts.ABrand Gear wheel 11a is driven by a motor 13 also mounted on main frame 12.

Rotatable member 9 may also, if desired, carry two compensating members 14 fixed thereto. These members are arranged to provide a substantially uniform absorption to radiation traversing body 4 along a plurality of parallel beam paths, such as are to be provided by the apparatus, despite the "circular" cross section of the body and surrounding material. Thus it may be ensured that detected variations of absorption are caused substantially only by variations in the body 4. Members 14 are mounted on member 9 so that they intersect the plane of the radiation.

Associated with detectors 3 there are provided collimators 15 arranged to define a plurality of substantially equiangularly spaced beams of radiation in the fan 2. As mentioned hereinbefore, a plurality of sets of parallel beam paths of the radiation through the body are to be provided. For this purpose source 1 and detectors 3, together with collimators 15, are arranged to move laterally relative to rotatable member 9. They are therefore arranged to move on bearings in respective tracks 16. In order to maintain their proper relationship the source and detectors are also joined by a lightweight but rigid yoke 17. Yoke 17 is constructed so that it does not interfere with the passing of radiation from source 1 to detectors 3 or with fixed members 14.

Also fixedly secured to the member 9 there is a reversible motor 18 which drives a toothed belt 19 by means of a drive shaft 20a journalled in member 9. The belt 19 also passes over an idler wheel 20b on a shaft also journalled in frame 9. The source 1 is thus subject to the required reciprocating lateral motion relative to member 9, and by means of yoke 17, the detectors 3 also execute that motion. A counter balance weight 21 is fixed to belt 19 opposite to source 1 to compensate for out of balance forces during the lateral movement. The relative motions are such that in this example 2.9° of rotation occur in the time of one lateral scan.

Also carried by yoke 17 there is a graticule 22 which is a translucent strip carrying engraved lines which interrupt light passing between a light source and photocell 23 fixed to a member 9. The signals obtained in response to the interruption are used by a computer controlling the processing to determine the positions of the source and detectors relative to the member 9 for respective data values obtained by the detectors. A similar graticule 24, scanning arrangement is designed so that each beam turns through an angle of 2.9°, in the course of a lateral scan, rather than 10° as in the previous arrangement.

It will be apparent that the set of beam paths thus provided for each beam of the fan does not represent a parallel set as assumed for the said convolution processing. However, it has been found that, if the total deviation from parallelism over the entire beam path set is restricted to the order of 3°, the convolution processing may be employed without modification and without significant error. The explanation for this is found in the nature of the convolution processing. Each beam path value, that is each signal representing the transmission of radiation along the respective beam paths, is modified by the addition of a term for each other beam path in the set. Each of those terms is moreover provided by mutiplying the value for the respective beam path with a factor related to the position of that beam path in the set relative to the beam path being modified. Thus the modifying terms for a beam path tend to be in inverse importance to the distance of the beam path providing them from the beam path whose value is being modified. The relevance of this can be seen in relation to FIG. 3 which shows a set of only seven beam paths at an exaggerated angular spacing. The beam paths are labelled 32 to 38. If the convolution processing is to be used to modify the absorption value for beam path 35 the maximum factors will be for beam paths 34 and 36, intermediate values for beam paths 33 and 37 and minimum for beams paths 32 and 38. However, it is beam paths 32 and 38 which deviate most from parallelism with beam path 35 and beam paths 34 and 36 which deviate least. Therefore, in terms of the processing, the error resulting from lack shown in part, is in the form of a ring fixed to member 9. This co-operates in similar manner with a photocell and light source 25, fixed to main frame 12 to provide information relating to the progress of the orbital motion for the same purpose.

The arrangement is such that, as source 1 and detectors 3 are scanned laterally, each detector provides an output signal indicative of the radiation incident thereon. These signals are amplified in a respective one of amplifiers 26 and integrated in a respective one of integrators 27 for an integration period determined by pulses from photocell 23. The signal thus provided by each integrator in one period represents a datum for a beam path incident on the respective detector and of width defined by the extent of the lateral motion in the integration period. The data are converted to digital form in converters 28 and to logarithmic form in converters 29 for provision at 30 to further processing which will be discussed hereinafter.

The apparatus so far described is, except in two respects, essentially the same as that disclosed in the said U.S. Pat. No. 3,946,234. The two differences are that motor 13 is arranged to provide a steady rotation of member 9, and the equipment mounted thereon, instead of an intermittent motion and that the angle through which the apparatus rotates in the course of one lateral scan is relatively less than the angular step of the previous arrangement. The rotation is normally of such an extent that the body is irradiated over a total angle of 180° but may be greater than that if desired.

Figure 2:
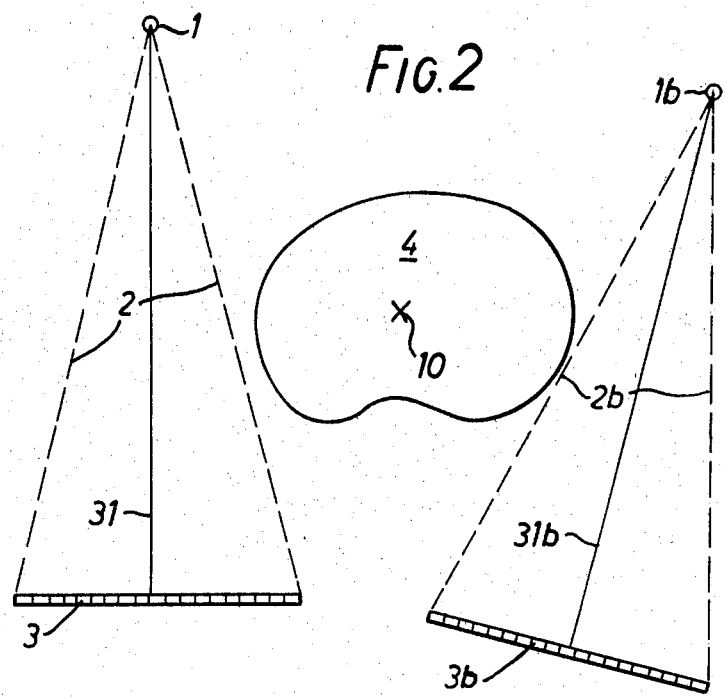
FIG. 2 illustrates the scanning motion employed.

FIG. 2 shows the scanning arrangement in simplified form for the purpose of illustrating the motions involved. The source 1 of radiation provides the fan-shaped spread of radiation indicated as before by the broken lines 2. It should be noted that, although the array of detectors is shown in straight line, the detectors may be arranged in arc, if desired, to be equidistant from source 1.

As mentioned hereinbefore, it is desired that each pencil beam of fan 2, typified by central beam 31, provides in effect, data for a set of parallel beam paths. In the apparatus of the said U.S. Pat. No. 3,946,234, the procedure is repeated at a plurality of orbital positions. For apparatus using the said convolution processing, data for each such parallel set is processed to give, for each beam path position in the set, a corrected value of absorption taking into account the values for other beam path positions. These corrected values are calculated so that, considering a small element of the planar slice of the body, the absorption coefficient for that element may be obtained with sufficient accuracy by suitable combination of the corrected values for all beam paths passing through that element. In practice, it is desirable that the beam paths pass through the centres of the chosen elements of the slice and interpolation is employed to take account of the fact that the beams do not, in general, fulfil this desideratum.

In the arrangement of the present invention, the continuous movement and a single lateral movement combined take the source to a position such as that shown in FIG. 2 at 1b. For that position the beam limits, detector array and centre beam are indicated by 2b, 3b and 31b respectively. It will be seen that in the course of one lateral movement the centre beam will have provided in effect a set of beam paths, across body 4, substantially equally spaced at a plurality of angular positions. For the preferred embodiment of the invention, which employs a fan of 30 beams of ⅓° spacing, the of parallelism is reduced by the low weighting of the most extreme values.

It is therefore arranged to apply convolution processing to the beam paths of each such set as if they were parallel, to provide the required modified values of beam path signals. If the slice is now divided into a notional matrix of elements, it is necessary to put into a location of the processing store for each element the modified values for the beam paths which pass sufficiently near to the centre of that element. To ensure that one such beam path exists for every set interpolation, such as that described in U.S. Pat. No. 4,002,910, is provided to give, for example, forty values between each pair of beam paths. Each value is stored at its appropriate position and allocated to those elements of the slice which are expected to be intersected by that beam path.

Although, for the example described hereinbefore in which the angular spread is small, the lack of parallelism of the beam paths does not significantly affect the convolution factors in general, it is true that the factors should be different for different spacings of beam paths. Since, in a fan-wise distribution, such spacings vary, the factors chosen for, say, the spacing as at the centre of the body will be in error for elements nearer to or further from the source. If the orbital scan is continued through 360° so that identical beam paths provide two absorption values irradiated in opposite directions, there is an opposite effect and residual errors are small. Otherwise, since the error can be calculated in advance for a known geometry, correction factors may be applied during computation.

It will be appreciated that the aforementioned technique of interpolation is not limited in its applicability to situations such as the one being described at present, where the angular spread of beam paths is small.

It will be understood that the motion of the source and detectors is determined by predetermined factors such as the geometry of the apparatus. Thus for any scan it will be known as a design factor what beam paths, through aperture 8, the radiation will follow. Thus the computer controlling the processing may be provided with the required information to properly allocate the data required to their positions in the matrix. Although variations may be provided in the scanning motion, such variations may also be programmed in advance into the computer. Nevertheless, for the purposes of better understanding of the invention a method for properly allocating the data, as derived, will be described.

To determine which beam path of the enlarged set, i.e. the set including the forty interpolated beam values between each two real beam values, should pass through any element, a method using a set of 'pseudo-beams' will be described. These pseudo-beams are arranged to cross the matrix of elements in zig-zag paths, intersecting element centre points, such that they approximately follow the path of the actual and interpolated beam paths. This is illustrated in FIG. 4 for a typical Cartesian matrix of elements of a slice. For clarity, the slice is shown to have a much reduced number of such elements than the practical embodiments. In FIG. 4 the region of interest is indicated by the circle 39. This has superimposed on it a matrix of elements, some of which are indicated by their centre points, such as 40. Seven pseudo beams are shown, only three in full. The beams are of equal length and are arranged so that together they intersect every element in the region of interest. Three of the real (non-parallel) beam paths of the set are indicated by lines 41, 42 and 43. It can be seen that the pseudo beams follow the general direction of the three beam paths shown. The other real beam paths of the set, together with the interpolated beam paths, have not been shown in FIG. 4 for the sake of clarity. The movements of the pseudo-beams from one element to the next are parallel to arbitrary axes x and y, the number of y steps in succession being $\Delta y$ and the number of x steps in succession being $\Delta x$. Each pseudo-beam is formed of a total of D x or y steps. For the pseudo-beams shown in FIG. 4 $\Delta y=2$, $\Delta x=1$ and $D=14$. Each pseudo-beam is characterised by particular values of $\Delta y$, $\Delta x$ and D. The pseudo-beams are used to determine the beam path of the interpolated set which passes closest to the centre of any particular element. The number appropriate to each beam path are functions of its distance along, that is position in, the set. A particular value of S is chosen to distinguish the required beam path. The value of S is set for the starting point $x_S$, $y_S$, of the first pseudo-beam which corresponds to one of the real beam paths of the set, and is updated for each step of the pseudo-beam. If the real beam path at the starting point makes an angle $\alpha$ with the y-axis the parameters $\Delta x$ and $\Delta y$ are set to give $\Delta x/\Delta y=\tan \alpha$ and the corrections for S to determine the number of the real or interpolated beam which passes through, or sufficiently close to, the centre of each element in turn along the pseudo-beam, are $(\delta x/\delta x)=\cos \alpha$ and $\delta s/\delta y=\sin \alpha$ where $\delta x$ and $\delta y$ are the increments in x and y from the last point reached by the last correction on S. S can therefore be updated by the value of $\delta s/\delta y$ or $\delta s/\delta x$ appropriate to the step being considered for each movement of the zig-zag pseudo-beam about the line of the real beam path. However, although the values of $\delta y$ and $\delta y$ are set so that the pseudo-beams follow the first real beam path of the set, that is hence the same mean direction, the other real beam paths for the same set will deviate from the nearest pseudo-beam if they are characterised by the same values of $\delta x$ and $\delta y$. If this is not corrected, at the ends of all but the first pseudo-beam there will be a deviation from the correct value of S for the real beam path, that is the choice of interpolated beam will tend to be incorrect. A correction is made for this as follows. If the real beam path at the end of the pseudo-beam is inclined to the y axis at an angle $\alpha f$, the change in S over the length of the pseudo-beam is $N \sin(\alpha - \alpha)$ where N is the number of elements in the x direction, equal to the number of beam path spaces, over which the pseudo-beam extends. Thus if the change is S is distributed equally over all of the steps of the pseudo-beam a correction $C = N \sin(\alpha - \alpha f)/D$ is obtained. Thus the total correction for each step is $\delta s/\delta x + C$ or $\delta y/\delta s + C$ for an x step or a y step respectively. As an alternative, corrections could be made to the values of $\Delta x$ and $\Delta y$ for each pseudo-beam.

In operation $\Delta x$ and $\Delta y$ are calculated, for the start of the first pseudo-beam for one beam path set, and $\delta s/\delta x$, $\delta s/\delta y$ and C evalauated. It will be appreciated that C will have a value of zero for the first pseudo-beam. As the pseudo-beam is followed values of absorption are obtained from the stored set of absorption values after interpolation, for each element of the matrix in response to the value of S calculated. These are added to the already stored absorption values for the respective elements. After D steps the next pseudo-beam is commenced using the same values of $\Delta x$ and $\Delta y$ but with the new value for C. After this procedure has been completed for every beam path, of every such set of beam paths in the complete orbital movement, the absorption values, stored in each element of the matrix, give the required representation of absorption for the slice.

As described, the values of $\Delta x$ and $\Delta y$ are set for the first real beam path of the set so that C has a value of zero for the associated pseudo-beam. However, it will be appreciated that $\Delta x$ and $\Delta y$ could be set for any of the real beam paths. If they are determined for a real beam path in the middle of the set, the deviation determining C can be distributed substantially equally about a centre value of zero.

The arrangement described uses forty interpolated absorption values for each pair of real beam paths of a set. The storage required to retain these values may be reduced by interpolating and then generating pseudo-beams for only, say, seven real beam paths at one time. The stored interpolated values would then be reduced in number to, in the present example, 280 values.

It will be appreciated that other systems may be employed for allocating the interpolated absorption values to their respective elements of the matrix.

FIG. 5 shows, in simplified block diagrammatic form, the organisation of data processing for the invention following log conversion in converters 29 as described in relation to FIG. 1. The digital data are first provided to a processing computer 44 where they are processed to provide data suitable for adding directly to the final matrix at the correct locations. As mentioned hereinbefore, this may conveniently be by the convolution method described in U.S. Pat. No. 3,924,129. The data are then in the form of corrected absorption values for individual beam paths, of each set of beam paths as shown in FIG. 3. In accordance with the principles of the invention, the processing is carried out as if these beams were in fact parallel.

The corrected beam values are then transferred to an interpolator 45 where they are processed, for example, as described in the said U.S. Pat. No. 4,002,910 to provide data for, say, forty interpolated beam paths equiangularly spaced between each pair of FIG. 3.

A computer comprising interpolator 45, or an additional computer, may also apply corrections for the relative spacing of the beams at the respective distance from the source. This may be by multiplying each entry in the matrix for a modified beam path through an element by a factor k/d where k is a constant and d is the distance of that element from the X-ray source for the source position originating that beam path.

The interpolated and possibly corrected data are then to be stored in a matrix store 46 equally at locations representing matrix elements through which or near to which the beam paths lie. This is achieved by an address selector 47 which provides the correct addresses for each data signal in a predetermined sequence in view of the known geometry of the apparatus. Alternatively, as described hereinbefore, the addresses may be allocated in response to data from photocell units 23 and 25, via the connections shown as broken lines.

It will be understood that although they have been shown in individual blocks, the functions of units 44 to 47 may be provided by a single digital computer.

The data from matrix store 46 are output to any suitable display arrangement for viewing as desired.

As previously mentioned, a considerable increase in data acquisition rate over and above the increase achievable by means of the apparatus shown in FIG. 1 can be achieved by following the procedures described and claimed in the aforementioned U.S. Pat. Nos. 4,035,647, 4,035,647 where a fan of radiation of sufficient breadth to span the body slice under examination is projected through the body and falls upon an extended array of detectors of sufficient breadth to accommodate the fan. In that case, the radiation source and the detectors are rotated synchronously around the body slice; the detector outputs being periodically sampled to permit the derivation of data indicative of the amounts of radiation emergent from the body slice along many substantially linear paths through the slice. In another techique permitting rapid data acquisition, to which the invention is also applicable, and as shown in FIG. 8, the detector array 74 is not merely sufficient to accommodate the fan 75 of radiation, but extends around the body slice 76 to an angular extent of at least 180°. The detectors 74 can then remain stationary while the source 77 alone rotates around the body slice. This technique is, of cource, more costly in terms of detectors and associated circuits, but it has certain advantages over techniques in which the source and detectors rotate around the body.

The most expeditious processing technique known at present is that described and claimed in the aforementioned U.S. Pat. No. 3,924,129. This, as has been stated already, involves a form of convolution of the acquired data.

It is clearly desirable to be able to use the rapid acquisition techniques just described in conjunction with the expeditious convolution processing technique of the aforementioned U.S. Pat. No. 3,924,129, despite the fact that said rapid acquisition techniques tend to produce data in groups relating to inclined paths followed by the radiation through the body slice. Such inclined paths can conveniently be described as a fan of paths and fans of paths can be considered as originating from the source or from individual detector devices, whichever is more convenient.

It is known that data acquired in fan beam geometry can be sorted into groups relating to parallel sets of paths prior to convolution processing. When this is done, however, it is found that the paths of each parallel set exhibit non-uniform spacing unless steps are taken to the contrary. In United States Patent Application Ser. No. 793,390 filed May 3, 1977, it is shown that errors introduced by the non-uniformity of spacing can be allowed for by the use of suitable multiplying factors generated by examination of a phantom body of known absorption characteristics. However, it is desirable to avoid this sorting procedure and to effect convolution directly on data relating to divergent fans of beam paths, and some complex mathematical procedures have been devised to this end. By way of example, the following documents are referred to as describing such complex mathematical techniques:
 1. Reconstruction from Divergent Ray Data by A. V. Lakshminarayanan (Technical Report No. 92) State University of New York at Buffalo, Department of Computer Science, January 1975.
 2. Tomographic Reconstruction from Fan Beam Geometry Using Radon's Integration Method by John W. Beattie (I.E.E.E. Transactions on Nuclear Science, Vol. NS-22, February 1975 pp. 359–363).

The following example of the invention aims at permitting data acquired in fan beam geometry to be processed by convolution without the need for either sorting into groups relating to parallel paths or complex mathematical procedures.

Referring now to FIG. 6, an X-ray source, for example a rotating anode X-ray tube 48, is mounted upon an apertured turntable 49 which rotates, in a suitable bearing not shown, relative to a static main frame 50. The aperture in the turntable 49 is shown at 51 and is dimensioned to accommodate the body of a human patient (not shown) lying supine or prone on an elongated table, or platter, shown at 52. The table 52 is supported by the main frame 50 and the floor of the building in which the apparatus is located, but the supports for the table are not shown in the drawing as they may take any of a number of convenient and well known forms.

Also shown is a disc 53 of uniform, or at least known, absorption properties and the disc 53 can be placed in the aperture 51, in place of the human patient, for a purpose which will become clear later. The disc 53 will hereinafter be called a "phantom" which is the terminology used in the art for such devices.

Mounted on the turntable 49, and disposed at the opposite side of the aperture 51 to the source 48, is an array 54 of radiation sensitive detectors. These detectors, in this example, are closely packed together and extend across the whole breadth of a fan-shaped distribution 55 of X-radiation generated by the source tube 48. The detectors can conveniently comprise scintillator crystals, such as sodium iodide or caesium iodide crystals, optically coupled to respective devices for converting visible radiation into electrical signals. These converter devices can be, for example, photomultiplier tubes or semiconductive photodiodes. In any event, each detector produces electrical output signals indicative of the amount of radiation received.

The turntable is rotated, by means not shown, around the patient position defined by the aperture 51 so as to cause the source 48 to follow an arcuate locus around the patient position whereby the body disposed at the patient position can be irradiated from many different directions. The output signals produced by the detectors are effectively sectioned up by an integration and resetting technique which will be described in more detail hereinafter, so that each output signal represents the amount of radiation projected through the patient position to a detector along a substantially linear beam path. The integration and resetting occurs a great many times during the rotation of the turntable around the patient position, and the integrators associated with all of the detectors in the array 54 are reset synchronously, so the effect is that, at each resetting instant, the array of detectors produces, in total, a group of output signals (one from each detector) relating to a group of divergent beam paths spanning the distribution 55 of radiation. The effect is substantially that of stopping the turntable 49 in a sequence of angular positions and of obtaining output signals while the turntable is stopped.

It will be appreciated that, since each output signal is required to relate to a substantially linear beam path through the patient position, it must not be contaminated by radiation which could, due to scatter of radiation within a body disposed at the patient position, reach the detector by other routes. For this reason, each detector views the source through a respective collimator, and an array of collimators is shown at 56. A source collimator 57 is also provided to ensure that the radiation conforms to the required fan-shaped distribution, and this collimator 57 preferably contains a beam splitting arrangement of the kind described and claimed in United States Patent Application Ser. No. 726050 to reduce spreading of the radiation in the direction perpendicular to the plane of the fan.

The progress of the rotation of the turntable 49 around the patient position has to be monitored, and to this end a graticule 58 of reflective or transmissive form and containing equiangularly spaced line markings is formed on the turntable 49 and co-operate in known manner with a photocell and light source assembly, generally shown at 59, mounted on the main frame 3, to produce electrical timing signals indicative of the motion of the turntable.

The timing signals derived from the assembly 59 are applied to a master timing circuit 60 which controls the operation of many of the circuit components now to be described.

An output signal connection $61r$ is shown as originating from the r'th detector in the array 54 and it will be appreciated that each detector in the array 54 has a separate output signal connection and that each such connection feeds a respective pre-processing circuit block, such as that shown at $62r$, containing, in series connection, an amplifier such as $63r$, an integrator circuit such as $64r$, an analogue-to-digital converter such as $65r$ and a logarithmic converter circuit such as $66r$. It will be appreciated that the integrator circuits such as $64r$ effect the sectioning up of output signals from the respective detectors which was referred to earlier, and that the resetting of the integrator circuits is effected in response to signals generated by the master timing circuit 60 under the control of the timing signals produced by the photocell/light source assembly 59.

All of the pre-processing circuits such as 62r feed a main convolution processing circuit 67 which can take any convenient form but preferably takes one of the forms described in the aforementioned U.S. Pat. No. 3,924,129. The processing circuit 67 produces, in known manner, values appropriate to each of a large number of elemental regions of a cross-sectional slice of the body disposed at the patient position and indicative of the absorption, of the radiation generated by the source 48 at those regions. These regions are commonly referred to as "pixels" and the values produces by the circuit 67 are applied to respective storage locations of a pixel value store 68. The store 68 has at least as many storage locations as there are individual pixels.

Successive groups of output signals from the array 54 of detectors are applied, as generated, to the processing circuit 67, and although, as mentioned previously, each group of output signals relates to a group of divergent beam paths through the patient position, the processing is effected as though the group related to a set of parallel beam paths at a suitable spacing, through the patient position. In essence, the processing involves modifying each output signal of each group by combining in a negative sense therewith, variously weighted components of the other output signals of the same group; the weighting being in accordance with a law, or function, which is monotonic and decreases in amplitude with increasing distance of the beam path giving rise to the output signal being weighted from the beam path giving rise to the output signal being modified. The full procedure is described in the aforementioned U.S. Pat. No. 3,924,129, the disclosure which is incorporated herein by reference.

Components of the modified output signals for each path are then distributed among the locations of store 68 appropriate to the pixels actually intersected by the beam path in question. Due account is taken, in known manner, of the fact that the beam paths intersect different pixels to different extents.

It will be appreciated that each pixel is intersected by a large number of beam paths and thus, as successive groups of output signals are applied to the circuit 67, values will accumulate in the storage locations of the store 68 which successively more closely approximate to the actual absorption values of the respective pixels. However, because as mentioned previously the convolution circuit 67 operates as if each group of output signals related to a set of parallel beam paths, and not the divergent paths followed in practice by the radiation (although as pointed out, the distribution of signal components to the pixel value store 68—known in the art as "back-projection"—is done in accordance with the actual divergent beam paths) some errors will exist in the pixel absorption values as finally evaluated.

In accordance with this example of the invention, these errors are eliminated, or at least reduced, by producing a series of multiplying factors, one for each pixel. These multiplying factors are derived by operating the apparatus in a calibration mode, selected by a switch 69, while the phantom 53 is disposed in the patient position. In the calibration mode, the apparatus works exactly in the manner described hereinbefore, but once the convolution processing is complete and the pixel value store 68 contains the best approximations to the pixel absorption values, these absorption values are compared, on a pixel-by-pixel basis, with the actual absorption values which are known to exist at the relevant pixels of the phantom.

This comparison stage can be effected automatically, as shown in the drawing, by providing a store 70, of identical form to the store 68; the store 70 containing the correct (known) absorption values for each pixel. Values for the same pixel are derived simultaneously from the two stores 70 and 68 and the former value divided by the latter in a dividing circuit 71 to obtain a multiplying factor for the pixel which is routed in the appropriate storage location of a multiplying factor store 72 which also has a storage location for each pixel. Multiplying factors for all of the pixels are obtained in sequence in the same way and it will be appreciated that each multiplying factor is dimensioned so that, when multiplied with the evaluated absorption value for a pixel, as stored in store 68, it produces the correct absorption value for the pixel, as stored in store 70.

Returning now to operation of the apparatus with a patient's body in the patient position, the values stored in the store 68 are multiplied, in a multiplying circuit 73, with the appropriate multiplying factors, and each corrected pixel value is then inserted into store 68 at the location previously occupied for the uncorrected value for the same pixel. Once this correction has been effected for all pixels, then the store 68 is connected to a video display unit which produces the aforementioned visual representation of the absorption values held in the store 68. The video display unit can be a complex console which includes a cathode ray tube display with photographic facilities, a numerical print-out and possibly other forms of display. Window-width (i.e. dynamic range) and window level (adjustment of centre value of range) can also be provided if required. Such controls are known in the art.

Hitherto, the extent of the rotation effected by the turntable 49 has not bee specified. There are special advantages to be had in rotating through 360°, thus irradiating the patient position along groups of beam paths symmetrically distributed around the body. If required, however, lesser amounts of rotation (such as 180°) can be used, provided that some residual errors can be tolerated due to the fact that (owing to the divergent nature of the beam paths in each group) the resolution will be higher on one side of the patient position (where the paths are closer together) than it will be on the other side of said position. Rotation through 360° overcomes that problem.

The angle of the distribution 55 of radiation can typically be 30° or more and a typical number of detectors is about nine per degree. Alternatively, of course, and as previously discussed in relation to FIG. 8 and shown, therein, the detectors need not rotate with the source in which case a large number of detectors may be arranged in a circle around the patient position. In that latter case, it will be appreciated that, as the source rotates relative to the detectors, each detector views in sequence a number of beam paths. These beam paths intersect at the detector, of course, and are distributed over a fan of angle determined by the angle of the distribution of X-rays produced by the source. In this case, it is possible to process the data in terms of fans originating from the source (as in the case described above) or in terms of fans notionally originating (but in fact terminating) at the detectors.

In practice, it is found that many of the multiplying factors are equal, or substantially so, and therefore the number of storage locations required in the multiplying factor store 72 can be substantially less than the number of pixels.

Instead of effecting the correction on a pixel-by-pixel basis after evaluation of the absorption values, it can be effected during the aforementioned stage of back-projection.

FIG. 7 shows a schematic flow diagram which may conveniently be used to summarise the operation of one example of the invention and which is believed to be self-explanatory.

As the multiplication of the evaluated pixel values by the appropriate multiplying factors is effected, in at least one example of the invention, at a late stage in the processing, it follows that the correction not only accommodates the errors caused by processing data relating to divergent beam paths as if they were parallel, but also corrects for other invariant sources of error in the apparatus. Examples of such other sources of errors are hardness variation across the distribution of radiation generated by the source 48 and hardness variations introduced by any shaped attenuators which may be disposed between the source and the patient position, and possibly also between the patient position and the detector array, to tend to equalise the absorption suffered by radiation over the whole distribution and despite the varying lengths of the different beam paths through the patient position.

It will be understood that the absorption values for the various pixels are measured, in each case, from a preselected datum level. That datum level is preferably the same for all pixel absorption values used or derived during operation of apparatus in accordance with the invention, as well as for the convolution processing operations.

What I claim is:

1. A medical diagnostic X-ray machine for examining a patient and for building up and displaying a two-dimensional picture of the X-ray response coefficients of the elements into which a slice of the patient, extending along a planar section through the patient, is divided by a finite Cartesian matrix superimposed on the slice, comprising:

means for deriving sets of output signals corresponding to sets of beam paths of finite lengths, each set of beam paths being made up of beam paths which substantially coincide with said section and have one of their ends at a common apex on one side of the patient and their other ends spaced from each other along the section at the opposite side of the patient to thereby form a fan-shaped distribution of beam paths, said apices being circumferentially spaced from each other along an orbit around the patient and at least the central beam paths of each of said sets of beam paths passing through the patient, each output signal being a measure of a response encountered by X-radiation in travelling along a corresponding one of said beam paths;

means for providing a sequence of convolution factors and means for producing, for each given one of said beam paths, a convolved output signal determined by accumulating: (1) the output signal corresponding to the given beam path weighted in accordance with a central factor of the sequence of convolution factors, and (ii) other output signals of the same set weighted in accordance with respective convolution factors the positions of which in the sequence correspond to the position of the respective output signals in the set;

means for providing a correction factor for each element of at least a substantial subset of the elements of said patient slice, said correction factors being measures of errors in producing said convolved output signals due to the fact that the beam paths of a set are in a fan-shaped distribution rather than being parallel to each other; and means for building up said picture by producing, for each element of the patient slice, an X-ray response coefficient based on the convolved output signals corresponding to the beam paths passing through the element, the respective positions of the last recited beam paths and slice element and the correction factor, if any, for the last recited slice element, and means for storing and for displaying said X-ray response coefficients to thereby display said picture of the patient slice examined by the machine.

2. A medical diagnostic X-ray machine as in claim 1 in which said means for producing said X-ray response coefficients comprise means for producing, for each slide element, a contribution for each beam path passing through the slice element, each contribution being based on the convolved output signal for the respective beam path and the relative positions of the beam path and slice element, and for weighting each of said contributions by the correction factor, if any, for the last recited slice element prior to said accumulating by the accumulating means.

3. A medical diagnostic X-ray machine as in claim 1 in which the means for providing said X-ray response coefficient for each slice element comprise means for providing and accumulating contributions based on each convolved output signal corresponding to a beam path passing through the slice element and the relative positions of the last recited beam paths and slice element, and means for weighting the total accumulation of all of said contributions by the correction factor, if any, for the last recited slice element after said accumulating by the accumulating means.

4. A medical diagnostic X-ray machine as in claim 1 in which the means for deriving the sets of output signals comprise means for producing a beam of X-radiation which originates at an origin orbiting at least half way around the patient, said beam being wide enough to encompass the entire patient slice, and means for detecting the X-radiation from the origin which has passed through the patient slice along said sets of beam paths and for producing said output signals based at least in part on the amounts of the radiation so detected by the detecting means along the respective beam paths.

5. A medical diagnostic X-ray machine as in claim 4 in which said detecting means comprise a ring of detectors extending along at least a half an orbit around the patient and disposed at the side of the patient opposite the orbit of the radiation origin to cause said detectors to view the radiation origin along said beam paths, said radiation origin moving with respect to the detectors while orbiting around the patient and each detector provide, at each given orbital position of the radiation origin, a signal on which a corresponding one of said output signals is based.

6. A medical diagnostic X-ray machine as in claim 5 in which the means for producing a beam of X-radiation comprise means for orbiting the radiation origin through a substantially full orbit around the patient and the detecting means comprise a ring of detectors surrounding the patient position substantially completely.

7. A medical diagnostic X-ray machine as in claim 4 in which the detecting means comprise a row of detectors disposed across the beam to view concurrently the radiation along each beam path of one of said sets of beam paths at each of a succession of orbital positions of the radiation origin, each detector providing a signal at each of said orbital positions of the origin which forms the basis of a respective one of said output signals.

8. A medical diagnostic X-ray machine as in claim 7 in which the detecting means includes means for causing relative motion between the radiation origin and the detectors in the course of said orbiting of the radiation origin.

9. Radiographic apparatus comprising a source of radiation projected towards a body, said radiation fanning out in one dimension as it proceeds away from said source to produce a flat, fan-shaped distribution of radiation which spans at least a substantial proportion of the extent of said body in said one dimension, scanning means for scanning said source angularly around said body to project radiation through said body from many different directions, detecting means for detecting the radiation emergent from said body along a group of mutually divergent, substantially linear paths from each of said directions and for producing corresponding groups of electrical signals indicative of the amounts of radiation emergent from the body along said groups of paths, processing means for processing the electrical signals corresponding to said groups of paths to produce a representation of the variation of absorption of said radiation with position over a cross-sectional slice of said body, and wherein said processing means includes means for combining each output signal with weighted components of other output signals of the same group as if they related to parallel beam paths, and compensating means, including a store of compensating factors each applicable to a respective region of such slice, evaluated during a preliminary operation of the apparatus with a body of known absorption characteristics, and means for combining evaluated absorption values for a body of unknown absorption characteristics with appropriate compensating factors prior to the production of said representation.

10. A medical diagnostic X-ray machine for examining a patient and for building up and displaying a two-dimensional picture of the X-ray response coefficients of the elements into which a slice of the patient, extending along a planar section through the patient, is divided by a finite Cartesian matrix superimposed on the slice, comprising:

means for deriving sets of output signals corresponding to sets of beam paths of finite lengths, each set of beam paths being made up of beam paths which substantially coincide with said section and have one of their ends at a common apex on one side of the patient and their other ends spaced from each other along the section at the opposite side of the patient to thereby form a fan-shaped distribution of beam paths, said apices being circumferentially spaced from each other along an orbit around the patient and at least the central beam paths of each of said sets of beam paths passing through the patient, each output signal being a measure of a response encountered by X-radiation in travelling along a corresponding one of said beam paths;

means for providing a sequence of convolution factors and means for producing, for each given one of said beam paths, a convolved output signal determined by accumulating: (i) the output signal corresponding to the given beam path weighted in accordance with a central factor of the sequence of convolution factors, and (ii) other output signals of the same set weighted in accordance with respective convolution factors the positions of which in the sequence correspond to the position of the respective output signals in the set;

interpolating means for producing in response to the convolved output signal of each set a substantially greater number of interpolated signals, corresponding to a fan-shaped distribution of beam paths substantially closer together than the beam path corresponding to the respective set of convolved output signals;

means for selecting from each fan-shaped distribution of closer beam paths the particular beam path which passes closest to the centre of each element of the slice, one such path being selected for every element of the slice;

a matrix store having locations respective representing the elements of the slice;

means for applying to each location of said store the signal corresponding to the beam path selected from each fan-shaped distribution of closer beam paths, being the path which passes closest to the centre of the element represented by the respective location, one such signal being applied to each location from every fan-shaped distribution of closer beam paths, thereby to build up the picture of the slice.

11. A method of examining a cross-sectional slice of a patient's body by means of penetrating x-radiation, the method including the steps of:

(a) acquiring data signals each indicative of absorption suffered by the radiation on traversing a respective substantially linear beam path across the slice; the beam paths conforming in total to a plurality of sets, each containing a plurality of mutually inclined beam paths distributed across substantially the whole cross-sectional dimension of said slice and the paths of each set being disposed at a respective mean angle in said slice;

(b) processing said data signals to produce a representation of the variation, from element to element over said slice, of absorption of said X-radiation;

(c) said processing step including the sub-steps of:

(d) modifying each data signal in turn by subtracting therefrom respective fractions of other data signals in the same set; the amplitude of said fractions being predicated upon the spacing between the beam path giving rise to the data signal being modified and the beam path giving rise to the data signal to be subtracted therefrom and also upon said spacing being uniform along the entire lengths of said beam paths, (e) deriving correction factors for the various elements, indicative of the error introduced by utilizing said fractions predicated upon uniform spacing in respect of beam paths which are mutually inclined and (f) utilizing the modified data signals and the correction factors to produce said representation.

* * * * *